US 9,480,852 B2

(12) United States Patent
Bonnamy (10) Patent No.: US 9,480,852 B2
(45) Date of Patent: Nov. 1, 2016

(54) EXTERNAL CARDIAC DEFIBRILLATOR SYSTEM FOR HOUSEHOLD USE (71) Applicant: SODAMED, Lourmarin (FR)

(72) Inventor: Jean-Marc Bonnamy, Marseilles (FR)

(73) Assignee: SODAMED, Lourmarin (FR)

( * ) Notice: Subject to any disclaimer, the term of this patent is extended or adjusted under 35 U.S.C. 154(b) by 0 days.

(21) Appl. No.: 14/383,608

(22) PCT Filed: Mar. 12, 2013

(86) PCT No.: PCT/FR2013/050512
§ 371 (c)(1),
(2) Date: Sep. 8, 2014

(87) PCT Pub. No.: WO2013/136005
PCT Pub. Date: Sep. 19, 2013

(65) Prior Publication Data
US 2015/0134018 A1 May 14, 2015

(30) Foreign Application Priority Data
Mar. 12, 2012 (FR) .................................. 12 52204

(51) Int. Cl.
A61N 1/39 (2006.01)
G09B 23/28 (2006.01)

(52) U.S. Cl.
CPC ........... A61N 1/3987 (2013.01); A61N 1/3968 (2013.01); A61N 1/3975 (2013.01); A61N 1/3993 (2013.01); G09B 23/28 (2013.01); A61N 1/3925 (2013.01)

(58) Field of Classification Search
USPC ............................................................ 607/5
See application file for complete search history.

(56) References Cited

U.S. PATENT DOCUMENTS

2003/0208237 A1* 11/2003 Locke et al. ...................... 607/5
2006/0173501 A1* 8/2006 Stickney et al. .................. 607/5
2007/0270909 A1 11/2007 Saketkhou
2009/0240297 A1 9/2009 Shavit

FOREIGN PATENT DOCUMENTS

WO 2006/104977 A2 10/2006
WO 2008/057302 A2 5/2008

* cited by examiner

Primary Examiner — Carl H Layno
Assistant Examiner — Jon Eric C Morales
(74) Attorney, Agent, or Firm — Jordan IP Law, LLC; Todd A. Vaughn (57) ABSTRACT External cardiac defibrillators that include automatic or semi-automatic self-contained defibrillators to be used by non-health professionals (physicians, nurses and other specifically trained persons). A power subassembly in an automatic or semi-automatic cardiac defibrillator system which, associated with a computer device, is capable of diagnosing a patient's condition by performing a simplified electrocardiogram, transmitting the data to the electronic device and supplying, controlled by this device, electric shocks to the patient, and also providing or contributing to further ancillary defibrillation functions.

15 Claims, 3 Drawing Sheets

Figure 3

EXTERNAL CARDIAC DEFIBRILLATOR SYSTEM FOR HOUSEHOLD USE

CROSS-REFERENCE TO RELATED APPLICATIONS

The present application is a National Stage Application of PCT International Application No. PCT/FR2013/050512 (filed on Mar. 12, 2013), under 35 U.S.C. §371, which claims priority to French Patent Application No. A 12 52204 (filed on Mar. 12, 2012), which are each hereby incorporated by reference in their respective entireties.

TECHNICAL FIELD

The invention relates to the field of external cardiac defibrillators, and more particularly automatic or semi-automatic self-contained defibrillators intended to be used for persons who are not health professionals (physicians, nurses and other specifically trained persons). It relates more particularly to a power subassembly in an automatic or semi-automatic cardiac defibrillator system which, associated with a computer device such as a computer, is capable of diagnosing the patient's condition, generally by performing a simplified electrocardiogram, transmitting the data to the electronic device and supplying, controlled by this device, electric shocks to the patient, and also providing or contributing to further ancillary defibrillation functions, such as for example the geolocation of the accident.

BACKGROUND

Defibrillation is a medical procedure for which the use was initially and legally reserved for physicians, either in a hospital environment or, using portable devices, on the site of the heart attack. It consists of applying by means of electrodes, to the chest of a patient suffering from "sudden death", generally caused by ventricular fibrillation, electric pulses or shocks of controlled duration, shape and intensity so as to restart normal cardiac activity.

Numerous external cardiac defibrillator systems intended to be used outside the hospital environment, by non-professionals, are now known. The difficulty is that of preventing an electric shock being emitted while the patient's heart is not in a state of tachycardia or ventricular fibrillation. In this way, a defibrillator intended to be used by non-professionals should be designed to restrict shock activation to this scenario, even if requested by the user (referred to herein as the "rescuer"). For this, the device records signals detected by the electrodes positioned on the patient in order to automatically establish a diagnosis (generally in the form of a simplified electrocardiogram) and decide on the appropriateness of discharging the electric shock.

A distinction is made between so-called semi-automatic defibrillators, wherein the rescuer needs to activate electric shock administration manually after moving away from the patient so as to no longer touch the patient, and so-called automatic defibrillators, wherein the electric shocks are sent automatically after a voice message has prompted the rescuer to move away. These automatic devices are furthermore increasingly widely used in public areas, and in companies.

Ventricular fibrillation results in certain death if defibrillation is not performed immediately. In France, it kills approximately 40,000 people a year. Each minute that passes is considered to lower the chances of survival by approximately 10%, given that after five minutes survival is accompanied by irreversible serious neurological damage. However, it is known that the majority of sudden deaths for which an external defibrillator could be used occur at the victim's home. The automatic or semi-automatic defibrillators intended for use by non-professionals existing on the market are not very suitable for household use for several reasons, including in particular the fact that they are too costly and insufficiently ergonomic. It is thus desirable to have more specialized devices for this household use which are simpler, less expensive, and more user-friendly, without making any sacrifices in terms of the performances thereof.

The prior art contains numerous documents describing the control of a defibrillator by a remote qualified person. By way of example, the U.S. Pat. No. 6,405,083 (Philips) describes a defibrillator capable of transmitting an electrocardiogram to a remote call center via a wireless link. Based on this information, a competent person will decide whether to perform defibrillation and sends the decision to the user on-site. Similarly, the US patent application 2004/020473 (Grath) describes the remote control of a defibrillator of a known type by a remote computer, via a wireless link. The U.S. Pat. No. 7,672,720 (Heath) describes an emergency medical device comprising an automatic defibrillator and further therapeutic and/or diagnostic functions (respiratory support, electrocardiogram recorder) and which is capable of communicating with an external computer. The U.S. Pat. No. 7,162,306 (MedTronic) and U.S. Pat. No. 6,321,113 (SurVivaLink) describe computer networking of a standard external automatic defibrillator.

The U.S. Pat. No. 6,148,342 (Cardiac Science, Inc.) describes a defibrillator which can be carried permanently by a patient at risk. This ensures maximum safety, the device being immediately available if required, but is however very restrictive and reserved for patients having a maximum risk as an alternative to implantable subcutaneous defibrillators. The document US 2009/0240297 (Shavit) describes a defibrillator electrode with a built-in electrical power supply and remote control receiver which can be activated remotely by a cellular telephone.

The document WO 2007/140142 (Saketkhou) describes the idea of integrating a defibrillator function in a cellular telephone. In view of the low capacity of cellular telephone batteries, this seems unfeasible in the current state of the art.

The problem addressed by the present invention is that of providing a self-contained external cardiac defibrillator that is simple, compact, lightweight, inexpensive, easy to use by non-professionals and which is designed specially with a view to household use with the choice of "automatic" or "semi-automatic" use.

SUMMARY

According to the invention, the problem is solved by separating the computer section and the communication interface with the user and the power section of the defibrillator system. In this way, the defibrillator system comprises a power subassembly essentially consisting of a self-contained electrical power supply and a circuit generating electric shocks and supplying same via electrodes to the patient, and optionally and accessorily ancillary devices for shaping the fibrillation detection signals or for the geolocation of the patient for the purposes of calls to external emergency services, said power subassembly being separable and separate from the computer device performing the control thereof and the communication with the user of the defibrillator, along with ancillary functions such as recording data, automatic calls to external emergency services, functional checking of the assembly, simulations, etc.

In this way, the power subassembly, which is preferably an integral assembly, is a peripheral of the computer device which, if applicable, receives therefrom instructions leading to the activation of at least one high-voltage electric pulse intended to be transmitted to the patient's heart via a plurality of electrodes positioned on the patient's body and connected by suitable means to the power subassembly.

More specifically, the first subject-matter of the invention is a cardiac defibrillator system, comprising: (a) a plurality of electrodes intended to be positioned on a patient's body to detect signals for establishing a diagnosis of the appropriateness of supplying an electric shock (for example a simplified electrocardiogram), and suitable for supplying electric shocks, and (b) a power subassembly, and (c) a programmable computer device, said computer device comprising: (i) means for exchanging data between said power subassembly and said computer device, and (ii) computing means and at least one memory unit, and (iii) means for communication (preferably two-way) with a human user present, and (iv) means for communication with a remote user or server, said power subassembly being separable from said computer device and said plurality of electrodes, and suitable for interacting with said computer device, and comprising (A) a self-contained, possibly rechargeable, electrical power supply, and (B) a power circuit for generating, shaping and supplying electric shocks to the patient, and (C) wired and/or wireless means for exchanging data with said computer device, and (D) means for connecting said plurality of electrodes, said cardiac defibrillator system being characterized in that said computing means of the computer device are programmed to analyze the diagnostic signals (particularly including the electrocardiogram) recorded and transmitted (optionally after conversion and/or reprocessing) by the power subassembly and to control if applicable the supply of one or a plurality of electric shocks to the patient by the power subassembly. The supply of one or a plurality of electric shocks to the patient may be activated by said human user present, or may be activated automatically.

In this cardiac defibrillator system, said power subassembly may further comprise at least one electronic circuit for converting and/or shaping the electrocardiogram or other signals detected on the patient, and used for diagnosing the appropriateness of supplying electric shocks.

Said system may also comprise geolocation means. It may also comprise means for storing electrical energy to compensate for a minimum time for a deficiency in the self-contained power supply of the computer device (for example when the battery thereof is discharged).

In one particular embodiment, said computing means of the computer device are programmed to deliver messages, particularly voice and/or visual messages, to guide the human user (rescuer) present in the positioning of the electrodes on the patient's body and optionally in the execution of further procedures to rescue the patient, such as performing a manual cardiac massage, and/or to perform a diagnosis of the appropriateness of supplying electric shocks to the patient, and/or to determine the electric characteristics of the electric shocks to be supplied, and/or to send to the power subassembly automatically or at the request of the human user the instruction to supply electric shocks, and/or to send a notification message to a remote user or server, optionally accompanied by information for locating said power subassembly; and/or to store in memory the diagnostic signals particularly including the electrocardiogram detected on the patient along with the characteristics of electric signals supplied to the patient, and/or to repeat the cycle until the patient is resuscitated, and/or to enable the simulation of the operation of the defibrillator so as to train a user on the use thereof, and/or are programmed to send, automatically or at the rescuer's request, a notification message to a remote user or server, such as a medical emergency service, optionally accompanied by information for locating said power subassembly. This information for locating the power subassembly may have been obtained by the geolocation means, and/or may comprise prerecorded messages.

In a further particular embodiment, said computing means are programmed to enable the training of the human user (rescuer) on the use of the device, and in particular on the positioning of the electrodes on the patient's body and as a general rule on the guidelines to follow under these circumstances; in particular said computing means may be programmed to help simulate the operation of the defibrillator.

The power subassembly comprises a device for storing electrical energy. Said subassembly may be powered on the mains, either with an integrated transformer or charger, or with an external transformer or charger which may be that of powering the computer device. Alternatively, it may consist of a non-rechargeable battery.

In one particular embodiment, the computer device is programmed so that the "defibrillator" function is immediately accessible if required. In the case of a computer for example at the time of the attack, said computer may be in three settings depending on whether it is switched off, on standby or in operation. In the first case, the procedure for starting up the device (sometimes referred to as the "boot" procedure) will take priority by setting to "defibrillator" before performing any other task such as installing the operating system or opening further programs; the user then has the choice of using the defibrillator or switching to the normal operating mode of the computer device. In the second case, setting to standby will automatically set to "defibrillator" so that it is immediately available on activation. In the third case, a combination of keys will make it possible to immediately invoke a defibrillation which will have loaded in the background on booting the device.

All these embodiments can be combined with each other.

A second subject-matter is a power subassembly in a cardiac defibrillator system, said cardiac defibrillator system comprising (a) a plurality of electrodes intended to be positioned on a patient's body to detect signals for establishing a diagnosis of the appropriateness of supplying an electric shock (typically a simplified electrocardiogram) and, more generally, and optionally, data such as impedance measurements for adjusting the shape and intensity of the electric shocks, and for supplying electric shocks, and (b) a power subassembly, and (c) a programmable computer device, said computer device comprising (i) means for exchanging data between said power subassembly and said computer device, and (ii) computing means and at least one memory unit, and (iii) means for communication (preferably two-way), preferably audio and/or visual means, with a human user present, and (iv) means for communication with a remote user or server, said power subassembly comprising: (A) a self-contained, possibly externally rechargeable, electrical power supply, and (B) optionally at least one electronic circuit for converting and/or shaping the electrocardiogram or other signals for diagnosing the appropriateness of supplying electric shocks, and for the characterization thereof (particularly shape and intensity), and (C) a power circuit for generating, shaping and supplying electric shocks to the patient via electrodes, and (D) optionally, geolocation means, and (E) means for connecting said electrodes, and said power subassembly being suitable for interacting with said computer device, and said power subassembly being characterized in that (1) it is separable from said computer device, and (2) it comprises wireless and/or wireless means for exchanging data with said computer device, and (3) it is suitable for detecting and transmitting (optionally after conversion and/or reprocessing) to the computer device the electrocardiogram or other signals used for diagnosing the appropriateness of supplying electric shocks and for the characterization thereof (particularly shape and intensity), and (4) it is designed to receive by means of the computer device the instruction to supply electric shocks to the patient via the electrodes, (5) it is suitable for supplying electric shocks to the patient via the electrodes.

A further subject-matter of the invention is a method for starting up a cardiac defibrillator system as described above, comprising the following steps: (i) the user present establishes an electronic connection between the power subassembly and the computer device and transports if required the assembly to the patient; (ii) the system checks the charge status of the electrical power supply of the self-contained electrical power supply of the power subassembly, and if this charge status is deemed to be satisfactory, the method continues with step (iii), otherwise, it sends a notification message; (iii) the computer device sends a message to guide the user present, particularly on the guidelines to follow and in particular on the positioning of the electrodes by the user on the patient's chest; (iv) the power subassembly records data for establishing a diagnosis of the appropriateness of activating, and optionally for characterizing, an electric shock, preferably an electrocardiogram, and optionally collects further data, such as impedance measurements to check the correct positioning of the electrodes and adjust the shape and/or intensity of the electric shocks, and sends these data to the computer device; (v) the computer device analyzes these data and decides whether an electric defibrillation shock is to be discharged by the power subassembly. It notifies the user of the decision thereof and gives further instructions on the basis of the diagnosed situation; (vi) After each electric shock, the device conducts a further diagnosis and cycle (iii) to (v) is repeated until the heart is restarted; (vii) In the event of ventricular fibrillation, the device calls the external emergency services automatically or at the user's request if this optional function has been installed. The data relating to the location may be included in this message if the geolocation option is available; (viii) In any case, the computer device stores in memory the data relating to the diagnosis and the log of electric shocks discharged. It may also send these data to a remote server.

In one embodiment, the computer program of the computer device compares the geolocation data supplied by the geolocation means of the cardiac defibrillator system to those contained in a database, and if the program finds in said database a location L corresponding to this location, the defibrillator system sends these data (or a portion of these data), optionally accompanied by a prerecorded message, by telephone, e-mail or the Internet, to a recipient, and preferably to an emergency service center, responsible for this location L. If the program does not find a location L corresponding to said location, the defibrillator system sends a message to an emergency service center using a prerecorded number.

A further subject-matter of the invention is a cardiac defibrillator system according to the invention, characterized in that it is suitable and designed for executing said method for starting up said system.

A further subject-matter of the invention is a method for simulating the use of the cardiac defibrillator system described above, in order to train and coach potential users, essentially reproducing the steps of the method for starting up the defibrillator system described above, except that the diagnoses are simulated (the correct positioning of the electrodes may however be checked on a real person), no electric shock is sent and no external call is made. In this way, such a method comprises the following steps: (i) the user establishes an electronic connection between the power subassembly and the computer device; (ii) the system checks the charge status of the electrical power supply of the self-contained electrical power supply of the power subassembly, and if this charge status is deemed to be satisfactory, the method continues with step (iii), otherwise, it sends a notification message; (iii) the computer device sends a message to guide the user, particularly on the guidelines to follow and in particular on the positioning of the electrodes by the user on the chest of the person acting as the patient in this simulation; (iv) the power subassembly records data relating to the cardiac activity of the person acting as the patient in this simulation, and preferably an electrocardiogram, and optionally collects further data, such as impedance measurements to check the correct positioning of the electrodes, and sends these data to the computer device; (v) the computer device analyzes these data and decides whether the quality of the data recorded would have been suitable for diagnosing the appropriateness of supplying electric shocks by the power subassembly.

It notifies the user of this decision and gives further information, particularly including one of the following items of information: (1) the information that the electrodes have been correctly or incorrectly positioned on the chest; (2) the information on how to trigger, in the simulation context, an electric shock as for a resuscitation scenario; (3) the information on repeating or improving the positioning of the electrodes on the chest, to repeat the simulation method in step (iv); and (4) the information on how to stop the simulation method.

A final subject-matter of the invention is a kit comprising the power subassembly according to the invention and accessories required or at least useful for using the cardiac defibrillator system, i.e. at least: a hydrogel receptacle and a razor; and more preferably also a towel moistened with a disinfectant.

DRAWINGS

FIGS. 1 to 3 illustrate embodiments of the invention, without limiting the scope thereof.

DESCRIPTION

The cardiac defibrillator system 1 according to the invention comprises a power subassembly 2, a computer device 3 and a plurality of electrodes 10, 11, i.e. at least two. The electrodes 10, 11 are not part of the power subassembly 2, but may be connected thereto by connection means 19, typically female connectors wherein male connectors acting as one of the ends of cables may be plugged, the other end of said cables being connected to the electrodes 10, 11 or formed thereby.

As a general rule, the power subassembly 2 according to the invention will only be used in the case of a heart attack, thus very rarely. A critical aspect of the cardiac defibrillator system 1 according to the invention is thus that of ensuring that, if required, the self-contained electrical power supply 15 of the power subassembly 2 is sufficiently charged to be able to supply a sufficient number of electric shocks with sufficient power. Advantageously, the power subassembly 2 comprises at least one visualization means, for example at least one indicator light. These visualization means may indicate satisfactory charging or, on the contrary, the insufficient charge status of the self-contained electric power supply 15, and/or the operating status of the power subassembly 2 or the defibrillator system 1. Furthermore, as described hereinafter, in one advantageous embodiment, the computer device 3 will send to each connection with the power subassembly 2 a request for information on the status thereof, particularly the electrical charge status thereof, in order to optionally trigger a notification if the status of the electrical power supply does not allow the supply of electric shocks.

The power subassembly 2 according to the invention may be optionally rechargeable externally. If the electric power supply 15 is rechargeable externally, it advantageously has connection means for charging said power supply 15.

In a first embodiment, the electric power supply 15 of the power subassembly 2 is recharged by an electric charger separate from that of the computer device 3. This charger may be external but in one particular embodiment is incorporated in said power subassembly 2. Said connection means may then be a power supply cable which is connected to the mains.

One advantageous arrangement consists of powering the computer device by or via the power subassembly. More specifically, one advantageous arrangement consists of powering the computer device via the power subassembly 2, requiring the user of the defibrillator to systematically recharge the battery of the power subassembly each time the computer device is recharged. In this case, a limitation of the power subassembly battery discharge level ensures that a minimum amount of power remains available in all cases for the proper operation of the defibrillator system.

In one alternative of this embodiment, said external electric charger may be that of said computer device 3.

In a second embodiment, the electric power supply 15 of the power subassembly 2 is recharged directly by the computer device 3. Said connection means may then be a power supply cable which is connected to a low-voltage output of said computer device 3.

In a fourth embodiment, the electrical power supply of the power subassembly 2 is a fuel cell integrated in said housing comprising at least one fuel tank, said fuel optionally being hydrogen. Said connection means may then be a nozzle for refilling said at least one fuel tank with fuel.

Regardless of the embodiment, the means for exchanging data 18 between the computer device 3 and the power subassembly 2 may be wired or wireless.

The power per shock supplied by the power subassembly 2 of the cardiac defibrillator system 1 is advantageously between 120 J and 350 J, it is preferably situated around 200 J. The number of such shocks suitable for being supplied without recharging the self-contained electrical power supply 15 thereof (and determining the capacity of this power supply) is at least 10 and preferably at least 30. It does not need to exceed 150. The generalized waveform is a conventional biphasic wave or any other form that progress in the art would tend to favor.

As mentioned above, it may be envisaged that the computer device 3 is powered by or via the power subassembly 2. In one alternative of this embodiment, the power subassembly 2 has a second battery, preferably rechargeable, which is dedicated for the power supply of the computer device 3, i.e. it does not supply power to the electrical power supply 15 of the power subassembly 2. This power supply of the computer device 3 by said second battery of the power subassembly 2 may be envisaged as a primary source or, preferably, as an auxiliary source, when a mains power supply of the computer device 3 is not available and when the self-contained battery thereof does not have a sufficient charge level.

Advantageously, the power subassembly 2 according to the invention comprises at least one storage space 21, such as a storage unit, for the electrodes 10, 11 and the accessories required or at least useful for using the cardiac defibrillator system 1, such as hydrogel receptacle, a razor, a towel moistened with a disinfectant, and for protecting same from dust and dirt.

Figure 1A:
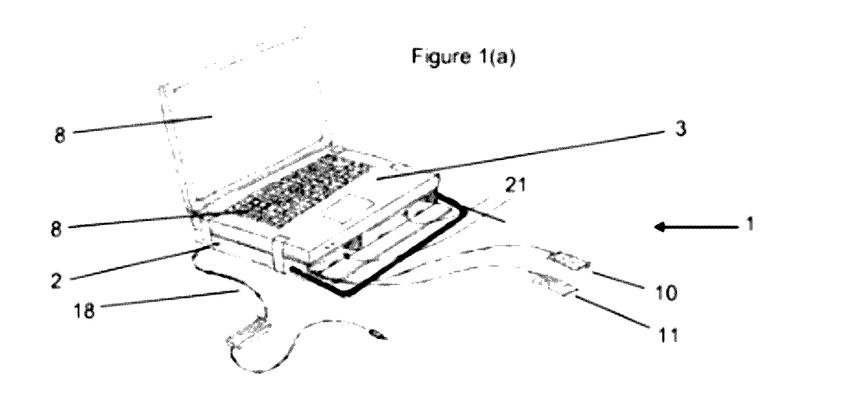
FIG. 1 shows schematically three embodiments of the power subassembly and the connection thereof to the computer device.
Figure 1B:
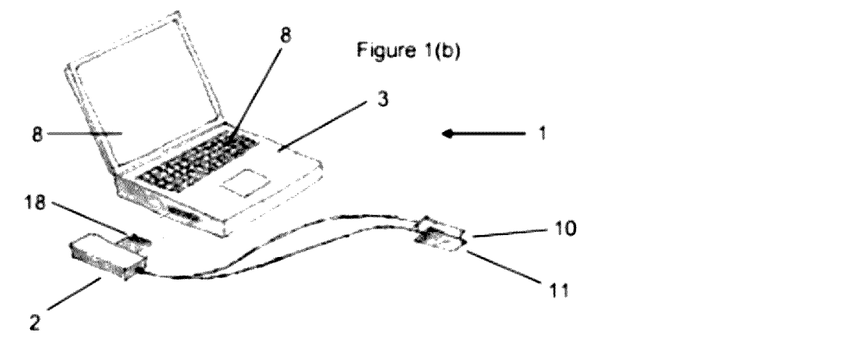
Figure 1C:
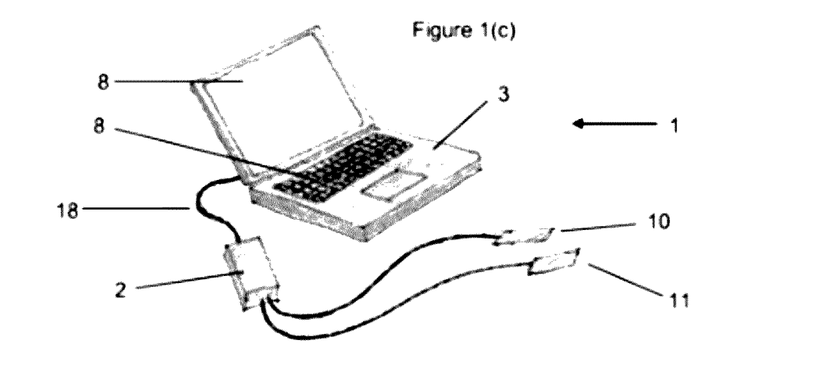

The computer device 3 may for example be a personal computer (PC), optionally portable (as illustrated in FIG. 1), or a cellular telephone, or a PDA (personal digital assistant), an IPOD™ and any other existing or future device having suitable computing means and interfaces, such as the communication interface 8 with the user present 13, enabling the user to enter and receive data and instructions. This interface should comprise display means (such as a screen) and/or a speaker, and means for entering data, such as a keypad or a touch screen.

According to the invention, the power subassembly 2 is "separable" from the computer device 3, i.e. the two components may be linked (connected) and separated (disconnected) very easily and without tools; in one particular embodiment, the power subassembly 2 is embodied in the form of a module suitable for being plugged into a connector of the computer device 3. This connection may simultaneously provide the physical, electronic and/or electrical link between the power subassembly 2 and the computer device 3. It may consist for example of a USB type connector, or a PCMIA card type connector, as illustrated in FIG. 1(*b*). Said computer link uses means for exchanging data 18 between the power subassembly 2 and the computer device 3.

The power subassembly 2 is advantageously an "integral" component, i.e. with the possible exception of the electrodes 10, 11, it is formed of one piece; this is important as the user is thus not liable to lose parts, given that it should be possible for the connection of the power subassembly 2 according to the invention to be made correctly even by a user in a state of stress or panic. The power subassembly 2 may be embodied in the form of a unit whereon the computer device 3 may be placed or mounted, as illustrated in FIG. 1(*a*). A mounting system may be envisaged to rigidly connect same to the computer device and facilitate the transport of the assembly to the patient.

It may be envisaged that the electrodes 10, 11 remain continuously connected to the power subassembly 2, i.e. cannot be disconnected easily by a user; this prevents the loss thereof, but it is all the same necessary to envisage being able to replace same if required, and particularly for conducting simulations.

Figure 3:
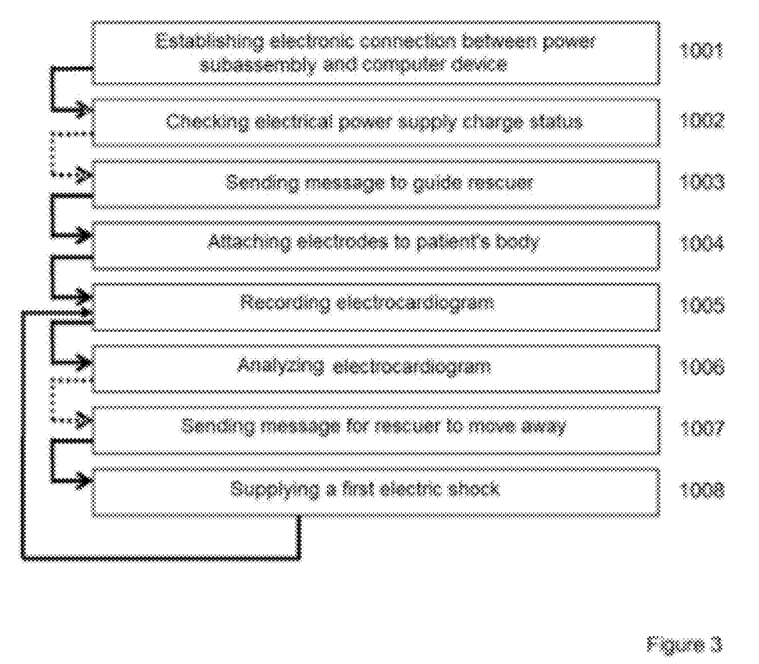
FIG. 3 shows schematically embodiments of the method according to the invention. The dotted arrows indicate that the transition to the next step is conditional.

As illustrated in part in FIG. 3, the human user present 13 establishes an electronic, electrical or physical connection (either wired or wireless) between the computer device 3 and the power subassembly 2 (step 1001).

It is advantageous that the human user 13 systematically establishes this connection whenever using the computer device 3. Furthermore, said device is advantageously designed to detect whether this connection has been established and, otherwise, make a notification on booting.

The computer device 3 sends a request to the power subassembly 2 to enquire on the status thereof (step 1002). This request may particularly relate to the charge status of the self-contained electrical power supply 15. The power subassembly 2 may be provided with a manual device (such as a button to be pressed) enabling the user present 13 to activate said request. On receipt of the request, the power subassembly 2 returns a message relating to the operating status thereof, comprising a message relating to the electrical charge status thereof. The processing of this response (and if applicable the activation of the request generating same) takes priority over any other user tasks executed by the computer device 3.

If the power subassembly 2 responds with a message indicating that the operating status is satisfactory (comprising a sufficient charge status of the self-contained electrical power supply 15), the computer device 3 executes an interactive program guiding the human user present 13 in the method intended to resuscitate the patient 12, using the man-machine interface 8 (step 1003). This interface may comprise means for communicating information to the user 13, typically visualization means (such as a screen) and/or a speaker, means for entering data by the user (typically a keypad or a touch screen or a microphone associated with speech recognition means). The program gives the human user 13 operational instructions, preferably step by step. They enable the user particularly to attach the electrodes 10, 11 at the correct locations on the body of the patient 12 (step 1004), after having suitably prepared the skin (particularly by shaving followed by applying a conductive gel) at the location where the electrodes 10, 11 are to be attached.

Subsequently, in step 1005, the cardiac defibrillator system 1 records and analyzes the data enabling the computer device 3 to diagnose the appropriateness of supplying electric shocks (typically a simplified electrocardiogram) and more generally, and optionally, data such as impedance measurements to check the correct positioning of the electrodes and adjust the shape and/or intensity of the electric shocks, and to supply electric shocks.

Then, in step 1006, the cardiac defibrillator system 1 analyzes said data and checks whether the patient's condition requires the supply of an electric shock. By way of example, if the analysis of the electrocardiogram reveals that the patient's 12 heart 4 is functioning normally, no shock is supplied and the rescuer is notified thereof. If the analysis of the data (and particularly of the electrocardiogram) in step 1006 reveals that the medical conditions for supplying an electric shock are met, the system 1, after notifying the rescuer, supplies an electric shock (step 1008) of a suitable shape and intensity via the electrodes 10, 11 and repeats the cycle until the awaited resuscitation of the patient 12 or the expiration of the potential survival period.

These shocks may be activated by the system 1 in semi-automatic mode, i.e. the system 1 prompts the user 13 to move away from the patient 12 (step 1007) and to activate (for example by pressing a key on the keypad of the computer device 3, or by pressing a button provided for this purpose on the power subassembly 2), the shock (step 1008).

They may also be activated in automatic mode, i.e. the system prompts the user, preferably via a speaker, to move away from the patient (step 1007) and directly activates the supply of the electric shocks (step 1008).

The analysis of the diagnostic data such as the electrocardiogram in step 1006 is performed by the computer device 3. For this purpose, the power subassembly 2 sends these data to the computer device 3. These data being analog, the so-called electrical circuit 16 for shaping the diagnostic signals advantageously comprises an analog/digital converter which converts same into digital signals to be sent by the means for exchanging data 18 to the computer device 3, unless said device accepts the analog signals 3 directly. The power subassembly 2 may also be designed to measure further parameters, such as the impedance between the electrodes 10, 11, which may enable the electronic device to detect incorrect positioning thereof or to adjust the shape and/or power of the electric shock to be supplied.

Figure 2:
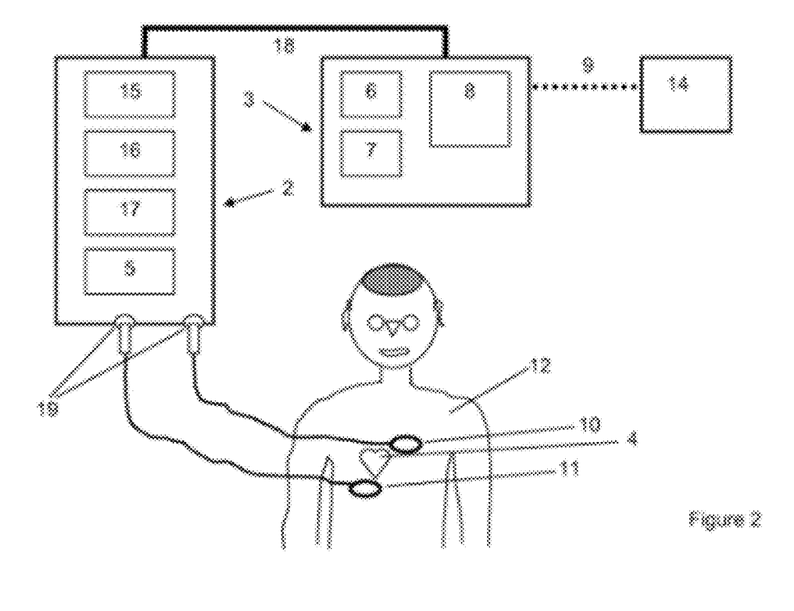
FIG. 2 shows schematically an embodiment of the cardiac defibrillator system comprising the power subassembly, the computer device and two electrodes positioned on a patient's body.

In one embodiment which may be combined with all the others, the computer device 3 is provided with means for communication 9 with a remote server 14, for example by the Internet or telephone. This remote server 14 may be a specific call center for handling medical emergency assistance requests, such as the SAMU in France, or it may communicate with such a center. Before triggering the electric shock, and/or after triggering same, the computer device 3 comes into contact with this remote server 14, and sends same automatically or at the rescuer's request one or a plurality of messages. This message may comprise:

- an element for identifying the incident (for example for identifying same as a heart attack, optionally by adding specific information for example the electrocardiogram),
- an element for locating the incident, preferably on the basis of geolocation data acquired in real time (i.e. when starting up the cardiac defibrillator system 1) by the geolocation means 5 contained in the power subassembly 2,
- optionally additional elements, for example the geographic address, the floor, and/or the building access code for the emergency service team, the person(s) to be notified in the event of an emergency, medical information for patients under treatment or taking particular medication, etc.

This message may comprise information on the technical status of a cardiac defibrillator system 1. In particular, if this status is such that the system 1 will not be capable of supplying a shock to the patient 12, this information should be transmitted particularly urgently, accompanied if applicable by information extracted from the patient's electrocardiogram, in order to enable the emergency service team to conduct a remote diagnosis of the cardiac condition of the patient 12. Similarly, if the computer device 3 decides that the diagnostic conditions have not been met to supply a shock to the patient 12 (for example because the patient's electrocardiogram does not show a state of ventricular tachycardia or ventricular fibrillation), the system 1 may send this information to the emergency service center for subsequent action in particular in the form of instructions to the rescuer which may be placed in communication with this center via the communication facilities of the computer device or by any other means.

The system according to the invention 1 may comprise geolocation means 5 capable of generating geolocation data. These geolocation means 5 may be found in a power subassembly 2 or, in one alternative embodiment, in the computer device 3. In one particular embodiment, the computer device 3 comprises a database typically managed by the buyer, owner or user of the power subassembly (or by any person keeping the subassembly in their home office in the event of the person themselves or a person present on the premises becoming a "patient" 12).

This database may comprise location information of at least one location ("L", for example the user's home, workplace, holiday home, the home of a close relative or friend) where the user is liable to be found with the power subassembly 2 at the time of the heart attack (for example: geographic address and/or geolocation coordinates of the location L), contact information (for example: telephone number of a close relative or a physician) and/or access information (for example for each location L: door number, building access code). It may also comprise personal and/or medical information on at least one person liable to become a patient 12 (for example: name of the person, name and contact information (particularly telephone number) of a person to notify, prescribed medication, allergies, major medical history).

This database may also comprise a prerecorded voice message in the national language corresponding to the location, accompanied by location information (defined above) and/or medical information (defined above). It may also comprise at least one telephone number for each location.

According to this embodiment, the computer program of the computer device 3 compares the geolocation data provided by the geolocation means 5 of the cardiac defibrillator system 1 to those contained in the database. If the program finds a location L corresponding to this location, it sends these data (or a portion of these data) to an emergency service center, responsible for this location L. Otherwise, the emergency call is routed to the closest service or a national number according to the specific organizations for each country or region, preferably by sending the geolocation data supplied by the geolocation means 5, optionally accompanied by a prerecorded message. The prerecorded message may be selected by the computer device accounting for said data relating to the location, such that the language of the message equates as much as possible with the language understood by the recipient of the message.

In one alternative embodiment, the geolocation coordinates of the location L that the user wishes to see included in said database may be entered automatically at the user's request by said geolocation means 5 when the user goes to the location.

The power subassembly 2 according to the invention may be used with any personal computer 3 of the standard type, and may advantageously remain continuously connected to this computer device. The system 1 is then provided with means enabling the user present 13 to activate the method for starting up the defibrillation system 1 immediately, without any significant delay relative to the constraint in respect of the rapidity of resuscitation. It may also be connected if required only, and for this scenario, the program of the computer device 3 is devised so as to ensure the priority and immediate execution of the method for starting up the system according to the invention. In this way, the investment cost required for fitting a household defibrillator system 1 according to the invention is limited to the power subassembly 2 and the program required to operate the computer device 3, on the assumption that a personal computer or another computer device 3 of the standard type already exists in the household or at the location wherein the system 1 is intended to be used (office, workshop, warehouse).

LIST OF REFERENCE NUMERALS

1: Cardiac defibrillator system
2: Power subassembly
3: Computer device
4: Patient's heart
5: Geolocation means
6: Computing means
7: Memory unit
8: Man-machine interface
9: Interface with remote server
10, 11: Electrode
12: Patient
13: Human user present
14: Remote server
15: Self-contained electrical power supply
16: ECG shaping electric circuit
17: Power circuit
18: Means for exchanging data
19: Electrode connection means
21: Storage space The four-digit references relates to steps of the method.

What is claimed is:

1. A cardiac defibrillator system, comprising:
a plurality of electrodes to be positioned on a body of a patient and to detect signals which establish a diagnosis of an appropriateness of supplying an electric shock, and which supply electric shocks;
a power subassembly having a self-contained, rechargeable, electrical power supply, and a power circuit to generate and supply electric shocks to the patient, a geo-location device, and a device to connect to said plurality of electrodes;
a computing device having a processor, at least one memory unit, and a first communication device to be used by a first party, a second communication device to be used by a remote user or server; and
a device to exchange data between the power subassembly and the computing device,
wherein:
said power subassembly is separable from said computing device and said plurality of electrodes, and
said processor of the computing device is programmable to analyze diagnostic signals, electrocardiogram, record and transmit, after conversion and/or reprocessing, by the power subassembly, and to control the supply of electric shocks to the patient by the power subassembly, and also programmable to compare geo-location data from the geo-location device to those contained in a database.

2. The cardiac defibrillator system of claim 1, wherein the device to exchange data comprises a wired device to exchange data.

3. The cardiac defibrillator system of claim 1, wherein the device to exchange data comprises a wireless device to exchange data.

4. The cardiac defibrillator system of claim 1, wherein the supply of electric shocks to the patient by said power subassembly is to be manually activated by said first party.

5. The cardiac defibrillator system of claim 1, wherein said processor of the computing device is further programmable to at least one of:
deliver messages to guide the first party in positioning the electrodes on the body of the patient and optionally executing further procedures on the patient;
perform a diagnosis of the appropriateness of supplying electric shocks to the patient;

automatically or manually send to the power subassembly a request by the first party an instruction to supply electric shocks;

send a notification message to the remote user or server, optionally accompanied by information to locate said power subassembly;

store in memory the diagnostic signals including the electrocardiogram detected on the patient and characteristics of the electric signals supplied to the patient;

repeat the cycle until the patient is resuscitated; and enable a simulation of an operation of the defibrillator so as to train a user on a use thereof.

6. The cardiac defibrillator system of claim 1, further comprising at least one electronic circuit to convert and/or shape the electrocardiogram or other signals detected on the patient, and which are to be used to diagnose the appropriateness of supplying the electric shocks.

7. A method to activate a cardiac defibrillator system, the method comprising:

providing a cardiac defibrillator system having a plurality of electrodes to be positioned on a body of a patient and to detect signals which establish a diagnosis of an appropriateness of supplying an electric shock, and which supply electric shocks; a power subassembly having a self-contained, rechargeable, electrical power supply, and a power circuit to generate and supply electric shocks to the patient, a device to exchange data, and a device to connect to said plurality of electrodes; and a computing device having a device to exchange data between said power subassembly and said computing device, a processor, at least one memory unit, and a first communication device to be used by a first party, a second communication device to be used by a remote user or server, wherein said power subassembly is separable from said computing device and said plurality of electrodes, and said processor of the computing device is programmable to analyze diagnostic signals, electrocardiogram, record and transmit, after conversion and/or reprocessing, by the power subassembly, and to control the supply of electric shocks to the patient by the power subassembly, wherein the computing device is programmable to compare the geo-location data to those contained in a database;

establishing an electronic connection between the power subassembly and the computing device;

determining a charge status of the electrical power supply of the power subassembly;

transmitting, via the computing device, a message to guide the first party, if the charge status is satisfactory;

recording data, via the power subassembly, to establish a diagnosis of the appropriateness of activating, and characterizing, an electric shock, for an electrocardiogram, and transmitting the data to the computer device; and analyzing, via the computing device, the data.

8. The method of claim 7, further comprising:

sending, via said computing device, data relating to a location of said power subassembly to a remote user or server.

9. The method of claim 7, wherein said data relating to the location comprises geo-location data and prerecorded data on said computing device.

10. The method of claim 7, further comprising, if the computing device finds in said database a corresponding location, sending the data to a third party recipient.

11. The method of claim 7, further comprising, if the computing device does not find in said database a corresponding location, sending a message to an emergency service center using the prerecorded data.

12. The method of claim 7, further comprising analyzing, via the computing device, the data to determine whether a quality of the data recorded would have been suitable to diagnose the appropriateness of supplying electric shocks by the power subassembly.

13. The method of claim 7, further comprising notifying the first party of the determination of the quality, and transmitting to the first party one of information relating to:

appropriate positioning of the electrodes on the patient;

administrating, in an simulation context, an electric shock;

repeating or improving the positioning of the electrodes; and ceasing the simulation.

14. The method of claim 7, wherein said data relating to the location comprises geo-location data.

15. The method of claim 7, wherein said data relating to the location comprises prerecorded data on said computing device.

* * * * *